(12) United States Patent
Jang

(10) Patent No.: US 9,616,218 B2
(45) Date of Patent: Apr. 11, 2017

(54) IMPLANTABLE PASSIVE MEDICAL LEAD

(75) Inventor: Grace Ying Yang Jang, Calabasas, CA (US)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 0 days.

(21) Appl. No.: 14/130,123

(22) PCT Filed: Nov. 4, 2011

(86) PCT No.: PCT/CN2011/081805
§ 371 (c)(1),
(2), (4) Date: Dec. 30, 2013

(87) PCT Pub. No.: WO2013/063798
PCT Pub. Date: May 10, 2013

(65) Prior Publication Data
US 2014/0180373 A1 Jun. 26, 2014

(51) Int. Cl.
*A61N 1/375* (2006.01)
*A61N 1/05* (2006.01)
*H01R 9/05* (2006.01)
*H01R 13/52* (2006.01)
*H01R 24/58* (2011.01)

(52) U.S. Cl.
CPC ............... *A61N 1/05* (2013.01); *A61N 1/056* (2013.01); *A61N 1/3752* (2013.01); *A61N 1/0573* (2013.01); *H01R 9/0518* (2013.01); *H01R 13/5224* (2013.01); *H01R 24/58* (2013.01)

(58) Field of Classification Search
CPC ....... A61N 1/3752; A61N 1/05; H01R 9/0518
See application file for complete search history.

(56) References Cited

U.S. PATENT DOCUMENTS 4,572,605 A * 2/1986 Hess .............................. 439/585
4,922,607 A 5/1990 Doan et al.
(Continued)

FOREIGN PATENT DOCUMENTS

CN 201329130 Y 10/2009
EP 1847290 A1 10/2007
(Continued)

OTHER PUBLICATIONS

International Search Report and Written Opinion in connection with International Patent Application No. PCT/CN2012/077783 filed Jun. 28, 2012. Apr. 4, 2013 (13 pages).
(Continued)

*Primary Examiner* — George Evanisko
(74) *Attorney, Agent, or Firm* — Kilpatrick Townsend & Stockton LLP

(57) ABSTRACT

A proximal end of an implantable lead may include a connector insulator having a center bore, a unitary connector pin fixedly disposed in the center bore of the connector insulator where the unitary connector pin includes a socket end configured for insertion into an electrical stimulation device and a conductor end electrically crimped to the first conductor, and a unitary ring connector having a band portion concentrically arranged around and insulated from the conductor end of the unitary connector pin and a crimp portion electrically crimped to the second conductor.

16 Claims, 13 Drawing Sheets

(56) References Cited

U.S. PATENT DOCUMENTS

| | | |
|---|---|---|
| 5,514,172 A | 5/1996 | Mueller |
| 5,741,321 A | 4/1998 | Brennen |
| 6,052,625 A | 4/2000 | Marshall |
| 6,183,305 B1 * | 2/2001 | Doan .................. A61N 1/3752 439/668 |
| 7,383,091 B1 | 6/2008 | Chitre et al. |
| 2011/0022144 A1 * | 1/2011 | Jarl ....................... A61N 1/056 607/127 |
| 2011/0220408 A1 | 9/2011 | Walsh et al. |
| 2012/0157810 A1 | 6/2012 | Doerr et al. |

FOREIGN PATENT DOCUMENTS

| | | | |
|---|---|---|---|
| WO | WO 2004/011081 A1 | 2/2004 | |
| WO | WO 2007/073435 A1 | 6/2007 | |
| WO | WO 2008/153451 A1 | 12/2008 | |
| WO | WO 2009/078752 A1 | 6/2009 | |
| WO | WO 2010/112245 A1 | 10/2010 | |
| WO | WO 2012/058547 A1 | 5/2012 | |

OTHER PUBLICATIONS

International Search Report and Written Opinion in connection with International Patent Application No. PCT/CN2012/077797 filed Jun. 28, 2012. Apr. 4, 2013 (11 pages).

International Search Report and Written Opinion in connection with International Patent Application No. PCT/CN2012/077806 filed Jun. 28, 2012. Apr. 4, 2013 (10 pages).

International Search Report and Written Opinion in connection with International Patent Application No. PCT/CN2011/081808 filed Nov. 4, 2011. Aug. 16, 2012 (11 pages).

International Search Report and Written Opinion in connection with International Patent Application No. PCT/CN2011/081799 filed Nov. 4, 2011. Aug. 16, 2012 (10 pages).

International Search Report and Written Opinion in connection with International Patent Application No. PCT/CN2011/081805 filed Nov. 4, 2011. Aug. 9, 2012 (10 pages).

\* cited by examiner

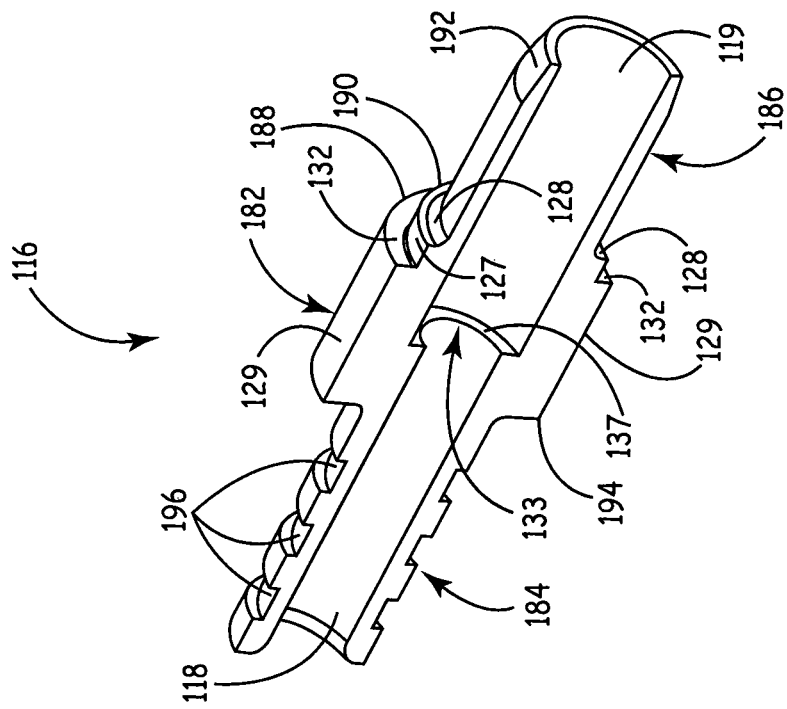
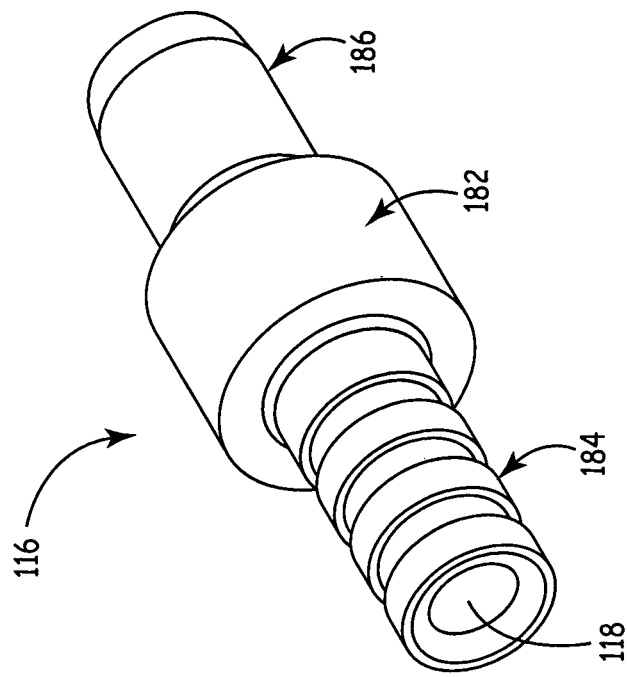
FIG. 6B
FIG. 6A

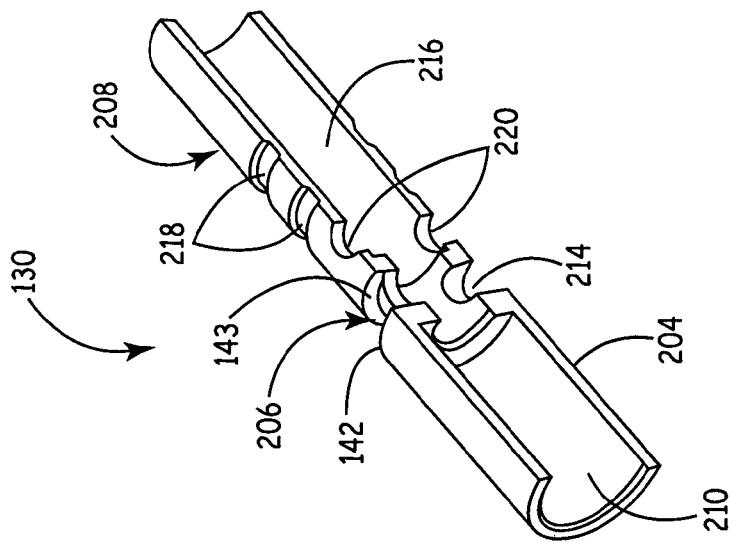
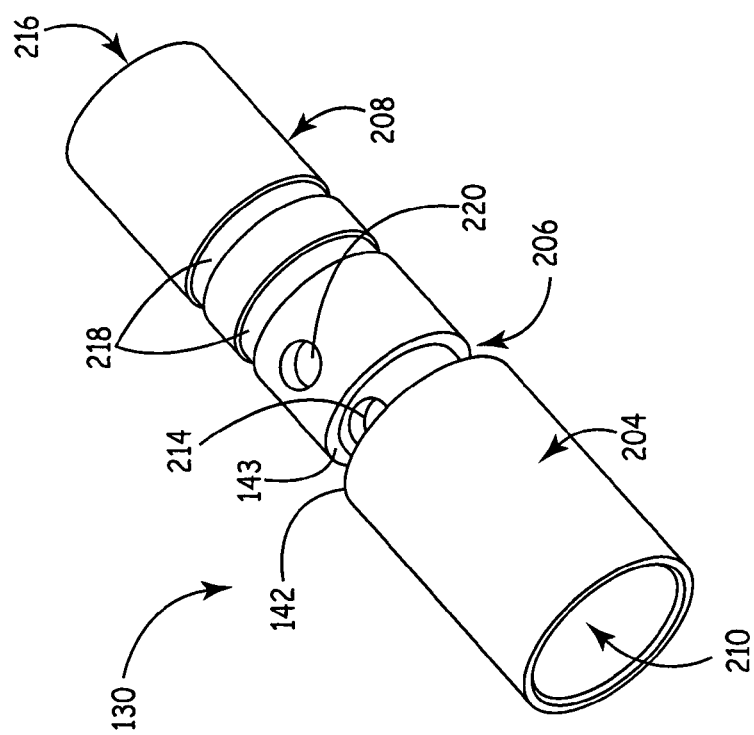
FIG. 8B
FIG. 8A

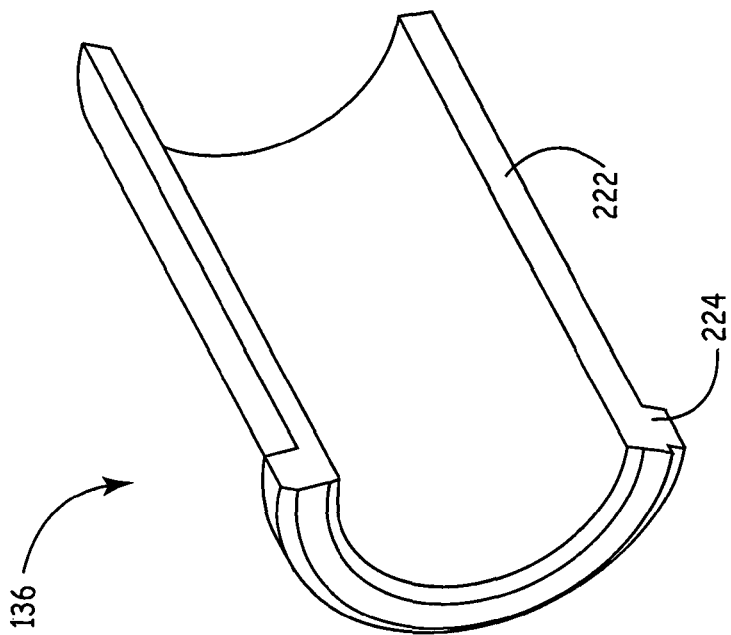
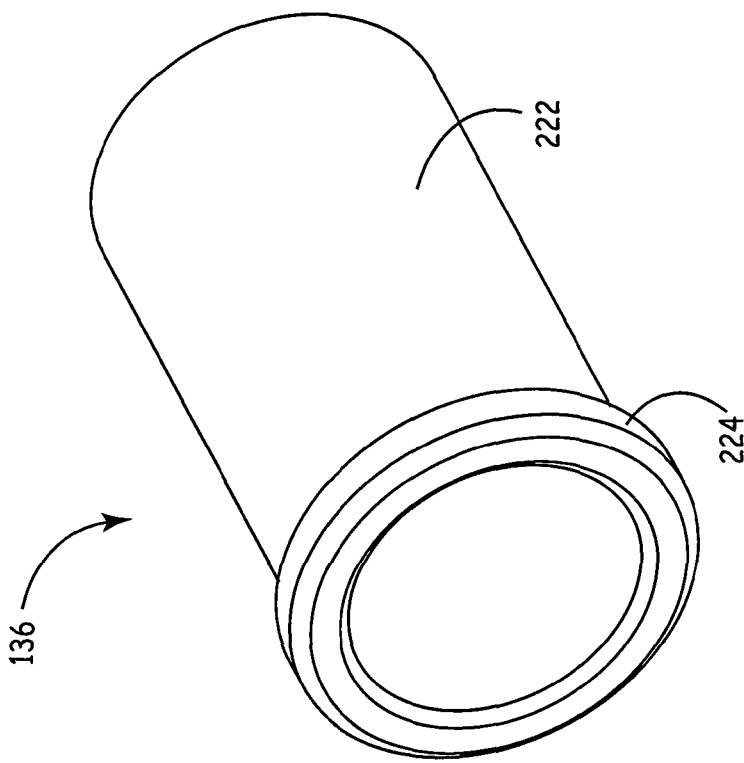
FIG. 9B
FIG. 9A

IMPLANTABLE PASSIVE MEDICAL LEAD

This application is a 35 USC 371 national stage of PCT Patent Application No. PCT/CN2011/081805, filed Nov. 4, 2011, entitled "Implantable Passive Medical Lead," the entire contents of which is hereby incorporated by reference, in its entirety.

FIELD OF THE INVENTION

The present disclosure relates generally to implantable electrical leads. More particularly, the present disclosure relates to connection end features of implantable electrical leads where the lead is connected to an associated defibrillator, pacemaker, or other electrical stimulation device. Still more particularly, the present disclosure relates to connection end features of implantable electrical leads having an active mechanism on a treatment end thereof.

BACKGROUND OF THE INVENTION

Electrodes are often used to stimulate contraction of the heart. For example, when a patient's heart is functioning with an abnormal rhythm, electrical energy may be applied to the heart via the electrodes to return the heart to a normal rhythm. In some cases this procedure may be an isolated event while in other cases a more frequent, regular, or even continuous process is used. In these cases electrodes may be incorporated into a lead that is used with a pacemaker, defibrillator, or other electrical stimulation device such that pacing pulses may be delivered, for example, to an atrium or ventricle of a heart. The system including the electrical stimulation device and the lead may be implantable and, thus, used over long periods of time.

In general, a lead includes a pair of electrodes disposed at a distal end of the lead which may be positioned in the right ventricle or the right atrium of the heart. The proximal end of the lead may be coupled to a defibrillator or a pacemaker and conductors may deliver electrical impulses along the length of the lead to the electrode thereby delivering pacing pulses to the heart.

There are at least two conventional types of leads. The first type of leads is referred to as an active electrical lead with an active mechanism at the distal end. The second type of leads is referred to as a passive electrical lead with a passive mechanism at the distal end.

The distal end of a typical active electrical lead may include a helix type fixation mechanism designed to be actuated and axially extend and/or rotate out of a tip portion of the lead to engage or embed into the endocardium. The distal end of a typical passive electrical lead may include an anchor type fixation mechanism designed to anchor the distal end in the heart. The fixation mechanism for a passive lead, for example, may include one or more radially spaced tines that secure the distal end in the heart.

The proximal end of pacemaker and defibrillator leads are commonly designed and manufactured to a standard such as YY/T 0491-2004//ISO 5841-3, 2000. The standard is applicable to both active and passive pacemaker or defibrillator leads. Within that standard, medical device implant companies commonly have their own unique designs. Among the technologies used to meet the standard, are laser welding and metal crimping resulting in highly reliable pacemaker and defibrillator lead joint connections.

The design of defibrillator and pacemaker leads has evolved over time. Over time and at present, the proximal end of an active electrical lead and the proximal end of a passive electrical lead are generally designed differently due to their functional differences. That is, the proximal end of an active lead may be designed to actuate and/or control the distal active mechanism, while the proximal end of a passive lead may not include such actuation and/or control features. System designs and assembly processes of the passive and active electrical leads are, thus, different. As a result, the overall cost of having significant different system designs and assembly processes is relatively high and a system having common features or similar or exchangeable components between an active electrical lead and a passive electrical lead may be less expensive and more attractive to consumers.

SUMMARY

In one embodiment of the present application, a proximal end of a lead may include a longitudinally extended, electrically conductive connector pin, extending through and fixedly disposed in a center bore of a proximal seal and a center bore of a connector insulator. The connector insulator may include a reduced section which extends within the center bore of the proximal seal. The proximal end may also include a longitudinally extended, electrically conductive inner coil crimped to the connector pin. The crimped connector pin and inner coil may be disposed within the center bore of the connector insulator and the connector pin may be electrically connected to the inner coil. The proximal end may also include a longitudinally extended, electrically conductive outer coil crimped to a ring connector and the ring connector may be electrically connected to the outer coil. The proximal end may also include a longitudinally extended insulator tubing disposed between the inner coil and the outer coil and the insulator tubing may provide electrical insulation between the inner coil and the outer coil and electrical insulation between the inner coil and the ring connector. The proximal end may also include a longitudinally extended boot seal disposed over the outer coil and the crimped outer coil and the ring connector may be disposed within a center bore of the boot seal.

In further embodiments, the proximal seal may include a plurality of seals to prevent fluid or other liquid from being in contact with the connector pin and may provide electrical insulation between the ring connector and the connector pin. Additionally in one embodiment, the boot seal may include a plurality of seals, wherein the boot seal prevents fluid from being in contact with the ring connector.

In one embodiment, an inner surface of the connector insulator may provide rotational bearing for the connector pin, and rotation of the connector pin may drive rotation of the inner coil. As such, rotation of the pin may result in rotating a mechanism disposed at a distal end of the lead. Such a lead may be referred to as an active lead, and the mechanism may be referred to as an active mechanism.

In another embodiment, the connector pin may be fixedly connected to an inner surface of the proximal seal by medical adhesive or other bio-adaptable adhesive. In this embodiment, the connector pin may not cause rotation of a mechanism disposed at a distal end of the lead. Such a lead may be referred to as a passive lead, and the mechanism may be referred to as a passive mechanism.

In still another embodiment, a proximal end of an implantable lead may be provided for use with a the lead having a first and a second conductor. The proximal end of the lead may include a connector insulator having a center bore and a unitary connector pin fixedly disposed in the center bore of the connector insulator. The unitary connector pin may include a socket end configured for insertion into an electrical stimulation device and a conductor end electrically crimped to the first conductor. The proximal end may also include a unitary ring connector having a band portion concentrically arranged around and insulated from the conductor end of the unitary connector pin and a crimp portion electrically crimped to the second conductor.

In yet another embodiment, an implantable medical electrical lead may include a longitudinally extended body having a distal end and a proximal end and a first conductor and a second conductor each extending from the distal end to the proximal end. The distal end of the lead may include a passive mechanism in electrical communication with the first conductor. The proximal end may include a unitary connector pin having a socket end configured for insertion into an electrical stimulation device and a conductor end electrically crimped to the first conductor. The proximal end may also include a unitary ring connector having a band portion concentrically arranged around and insulated from the conductor end of the unitary connector pin and a crimp portion electrically crimped to the second conductor.

One of the advantages of the embodiments disclosed herein is that most of the parts and components of active and passive leads can be shared. As such, while the several parts of the passive lead may be more involved or complicated than other passive lead designs, the commonality between the parts of the active lead and passive lead may reduce the cost of tooling, manufacturing, and assembly for a manufacturer that is manufacturing both active and passive leads. By reducing the differences between the two types of leads, the savings in manufacturing the leads may make up for any costs associated with a more complicated passive lead design.

BRIEF DESCRIPTION OF THE FIGURES

FIGS. 6A and 6B show a perspective view and a perspective cross-sectional view, respectively, of a connector insulator of the lead of FIG. 1.

FIGS. 8A and 8B show a perspective view and a perspective cross-sectional view, respectively, of a ring connector of the lead of FIG. 1 and FIG. 2.

FIGS. 9A and 9B show a perspective view and a perspective cross-sectional view, respectively, of a ring sleeve of the lead of FIG. 1 and FIG. 2.

DETAILED DESCRIPTION

The present disclosure relates, in one embodiment, to an implantable electrical lead having an active mechanism on a distal end for engaging the heart or other treatment site of a patient. (i.e., active lead) In another embodiment, the present disclosure relates to an implantable electrical lead having a passive mechanism on a distal end. (i.e., passive lead) Each of the active and passive leads may include a system of parts on a proximal end thereof that is primarily adapted to connect to and electrically communicate with a defibrillator, pace maker, or other electrical stimulation device. It is noted that some of the parts may be adapted to insulate between other parts and/or between the proximal end and the electrical stimulation device. In the case of the active lead, a portion of the parts may be particularly adapted to allow actuation and control of the active mechanism on the distal end of the lead while others of the parts may be more generic for use with active or passive leads. In contrast, the passive lead, while including the generic parts, may include a portion of parts particularly adapted to restrain relative motion of the parts and thus avoid provisions for actuation and control. In some embodiments, the systems of parts of the proximal end of the leads may be designed such that few parts differ when comparing the parts of an active lead to the parts of a passive lead. As such, a relatively high number of parts may be the same between active and passive leads.

Figure 1:
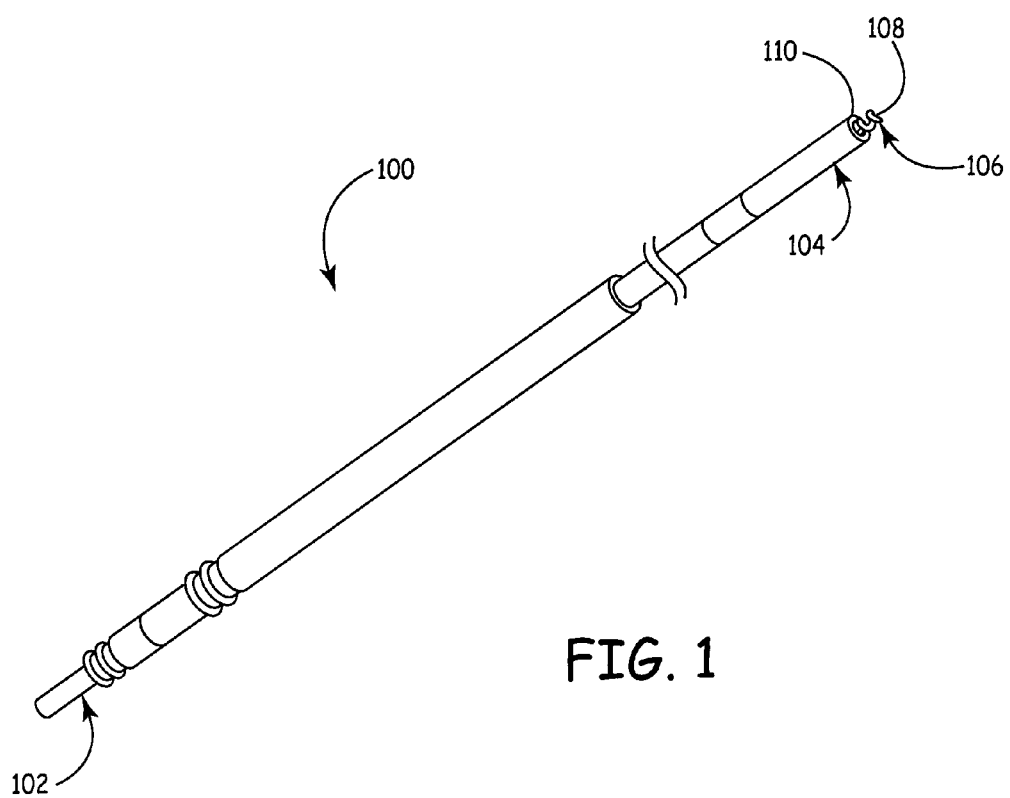
FIG. 1 shows a perspective view of one embodiment of an implantable medical electrical lead with an active mechanism according to some embodiments.

FIG. 1 illustrates a perspective view of one embodiment of an implantable medical electrical lead 100. The lead 100 has a proximal end 102 and a distal end 104. As shown, an active mechanism 106 may be disposed at the distal end 104 and may include a helix-type fixation mechanism 108. The fixation mechanism 108 may be designed to axially extend out of a tip portion 110 of the lead 100 to engage a treatment site of a patient such as the endocardium of a heart, for example. The helix-type of fixation mechanism 108 may be retractably extended out of the tip portion 110 at the distal end 104 of the lead 100. In operation, a conductive connector pin at the proximal end 102 of the lead 100 may be rotated to drive the active mechanism 106 at the distal end 104 of the lead 100, thereby extending the helix-type fixation mechanism 108 out of the tip portion 110 of the distal end 104 of the lead 100. The rotating extension of the helix-type fixation mechanism 108 may cause the mechanism 108 to engage (i.e., screw into) a treatment site of a patient.

Figure 2:
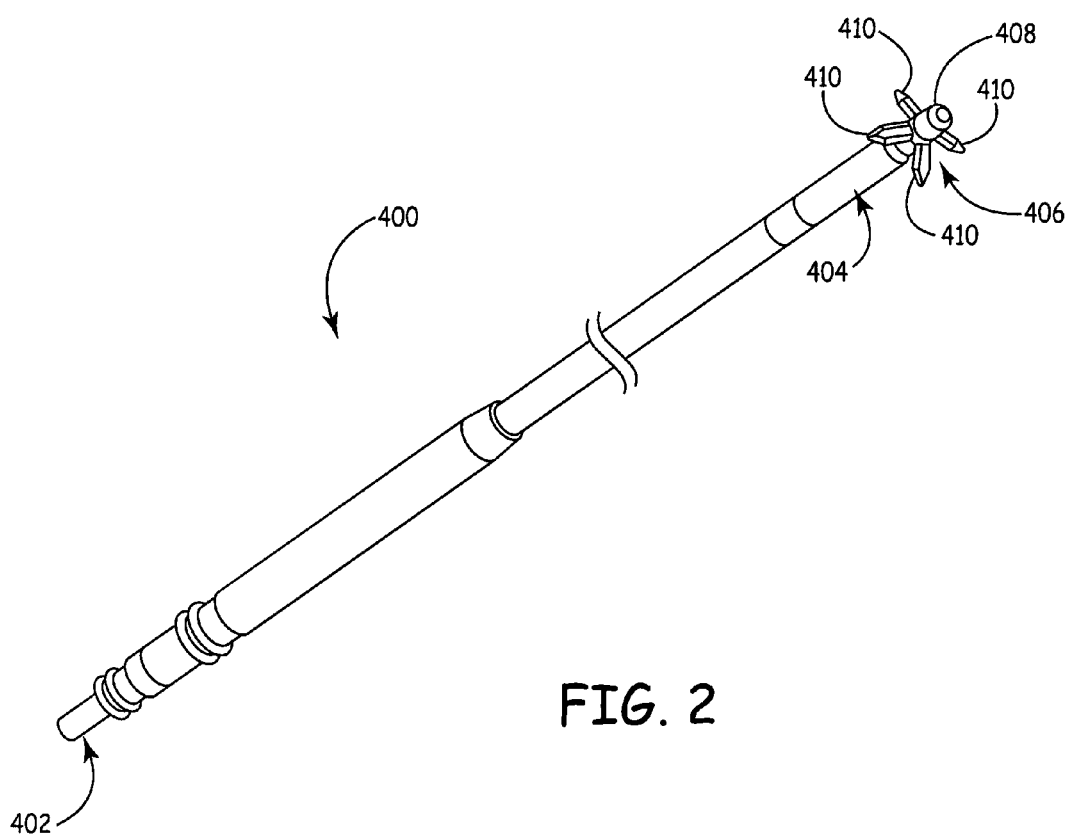
FIG. 2 shows a perspective view of one embodiment of an implantable medical electrical lead with a passive mechanism according to some embodiments.

FIG. 2 illustrates a perspective view of another embodiment of an implantable medical electrical lead 400. The lead 400 has a proximal end 402 and a distal end 404. As shown, a passive mechanism 406 may be disposed at the distal end 404 and may include an anchor-type fixation mechanism 408. The fixation mechanism 408 may be designed to anchor the lead at a treatment site of a patient such as the endocardium of a heart, for example. The fixation mechanism 408 may include one or more radially spaced tines 410 that engage the treatment site or other tissues adjacent to the treatment site thereby holding the distal end at or near the treatment site.

As shown in FIGS. 1 and 2, the lead 100 is longitudinally extended between the distal end 104 and the proximal end 102, and the lead 400 is longitudinally extended between the distal end 404 and the proximal end 402. It is appreciated that the primary focus of the present invention is the proximal end 102,402 of the lead 100,400 whereas the distal end 104,404 of the lead 100,400 can be of any suitable fixation mechanism as described above in FIGS. 1 and 2, without departing from the principles of the present invention. It is also appreciated that the proximal ends 102,402 of the leads 100,400 are designed and arranged such that most of the parts or components of the leads 100,400 can be commonly used. That is, an overall product line or system architecture approach has been used in the design to consider the tooling, manufacturing, and assembly implications of the selected designs. As a result, the designs of active leads 100 and passive leads 400 are more similar to one another than other active and passive leads in the art. Accordingly, the overall cost of manufacturing such leads may be significantly reduced.

Figure 3:
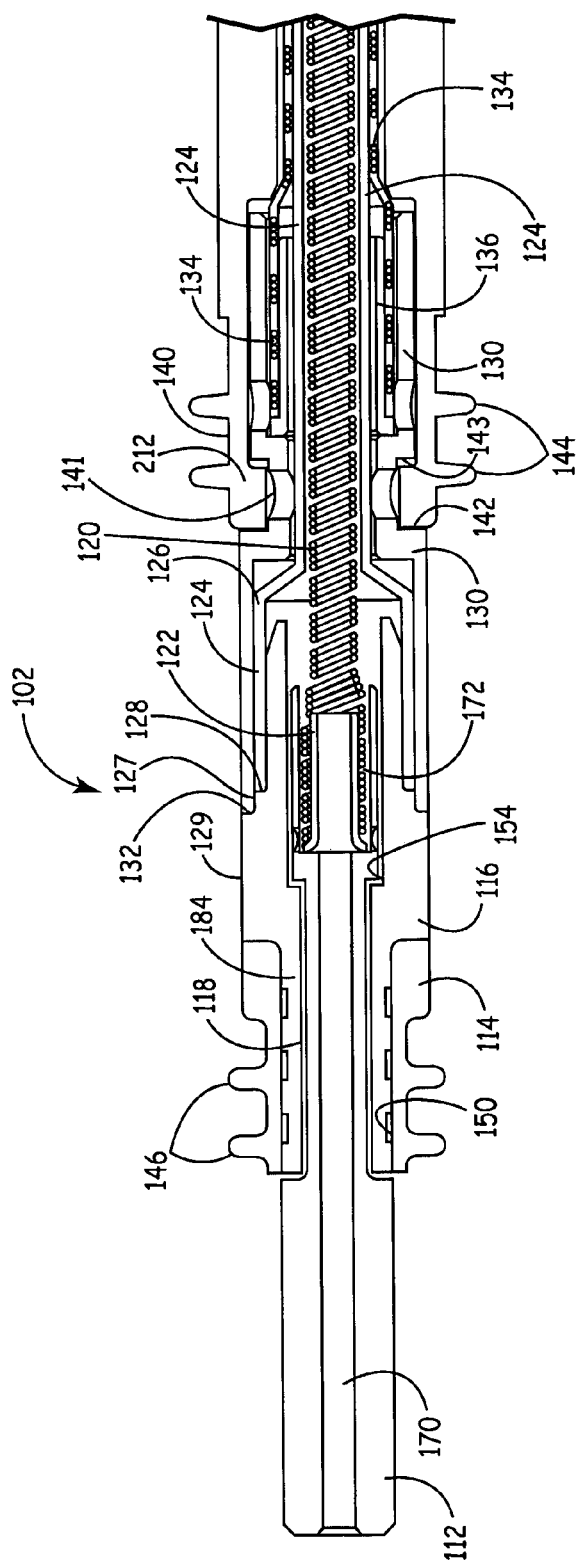
FIG. 3 shows a cross-sectional view of a proximal end of the lead of FIG. 1.

Referring now to FIG. 3, the proximal end 102 of the lead 100 includes a system of parts or pieces. The system of parts or pieces may be divided into three categories including inner parts relating to an inner conductor, outer parts relating to an outer conductor, and insulating parts for electrically separating the inner parts from the outer parts. The inner parts may include a conductive connector pin 112, an inner conductor or coil 120, and a pin sleeve 122. The outer parts may include a ring connector 130, an outer conductor or coil 134, and a ring sleeve 136. The inner and outer parts may be substantially separated by the insulating parts including a connector insulator 116 and an insulator tubing 124. A proximal seal 114 and a boot seal 140 may also be provided.

Beginning with the inner parts, the connector pin 112 may be configured for electrical engagement with a defibrillator, pacemaker or other electrical stimulation device and for communicating electrical impulses to the inner conductor or coil 120. As such, the connector pin 112 may be adapted at one end for plugging into a socket of an electrical stimulation device and may be adapted at another end for connecting to the inner conductor or coil 120.

Figure 4:
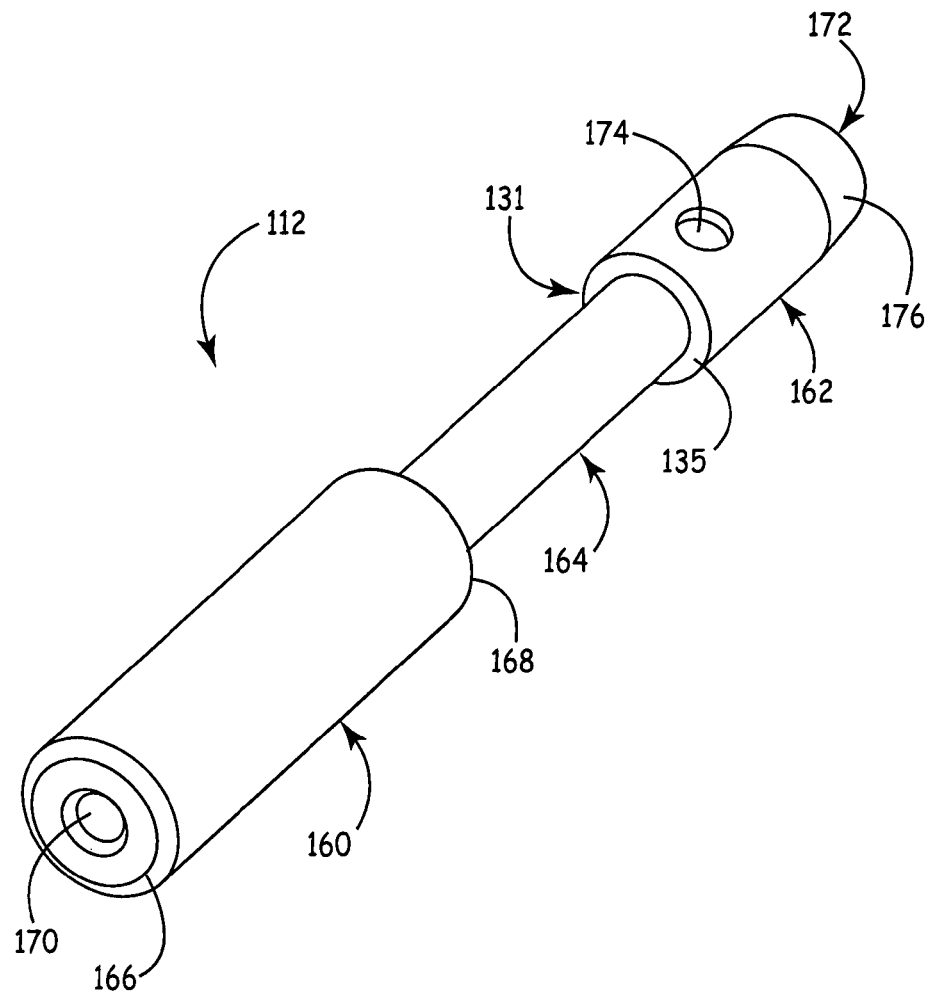
FIG. 4 shows a perspective view of a connector pin of the lead of FIG. 1 and FIG. 2.

A close-up view of a connector pin 112 is shown in FIG. 4. As shown, the connector pin 112 may include a socket end 160 and a conductor end 162 and may further include a necked-down portion 164 extending therebetween. The socket end 160 of the pin 112 may be generally elongate and cylindrically shaped and may have a diameter adapted for placement in a correspondingly shaped socket of an electrical stimulation device. The proximal end of the socket end 160 may include a chamferred edge 166 for guiding the pin 112 into the socket when placing the pin 112 into the electrical device. The distal end of the socket end 160 may include a substantially sharp or square edge 168 for abutting the connector insulator 116 or the proximal seal 114 as the case may be.

With respect to exposed portions of the proximal end of the lead, like the socket end just described, that may contact or otherwise physically interact with an electrical stimulation device, these portions may be designed to meet industry standard specifications such as the IS-1 specification, for example. As such, while particular parts of the proximal end are described herein as varying in size, diameter, length, or other dimensional variations, in some embodiments, the exposed portions of the parts may be selected to meet such specifications or standards. However, nothing in the present disclosure should be construed to limit the parts to industry standard dimensions.

Figure 11:
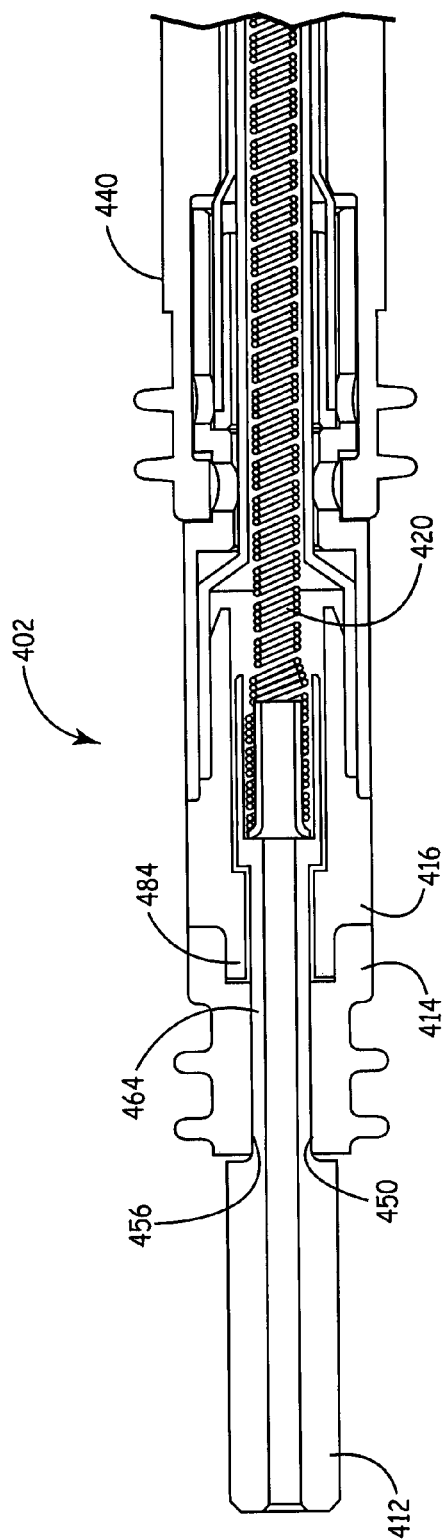
FIG. 11 shows a cross-sectional view of a proximal end of the lead of FIG. 2.

The necked-down portion 164 of the connector pin 112 may also be generally elongate and cylindrically shaped an may have a diameter smaller than that of the socket end 160. The necked-down portion 164 may have a length selected to longitudinally secure the pin 112 relative to the connector insulator 116 and the proximal seal 114. That is, the length of the necked-down portion 164 may correspond to a bore length in the connector insulator or, as shown in FIG. 11, a bore length in the connector insulator plus a bore length in the proximal seal, such that longitudinal motion is substantially prevented relative to the connector insulator and the proximal seal. This particular aspect of the connector pin design may contribute to allowing for the same pin 112, 412 to be used in both the active and passive lead designs. As shown in FIG. 3, the socket end 160 and the necked-down portion 164 may include a longitudinally extending bore 170 extending from the proximal end of the pin 112 to the distal end of the necked-down portion 164 and exiting into a crimp zone 172 within the conductor end 162 of the pin 112. This bore 170 may be sized and adapted to receive a stylet, for example, when installing or positioning the lead, or when access to the distal end of the lead is desired.

The conductor end 162 of the pin 112 may be substantially cylindrically shaped with an outer diameter slightly larger than that of the necked-down portion 164 and slightly smaller than that of the socket end 160. Other relationships of diameters of the several portion of the connector pin 112 may also be provided. For example, the conductor end 162 may have an outer diameter larger than the socket end 160. In the embodiment shown, however, for example in FIG. 3, the conductor end 162 may be arranged in a relatively congested area where the ring connector 130, the insulator tubing 124, the connector insulator 116, the conductor end 162, the inner conductor 120, and the pin sleeve 122 all overlap. Where the proximal end is designed to meet the IS-1 specification, for example, restrictions on the overall outer diameter together with the congestion may cause the outer diameter of the conductor end 162 to be smaller than the socket end 160. The conductor end 162 of the pin 112 may include an inner cavity or crimp zone 172 having a substantially cylindrical cross-section with a diameter defining an inner diameter of the conductor end 162. The conductor end 162 may have a length selected to match or exceed the length of the pin sleeve 122, to be described below, so as to provide suitable length for crimping the conductor end 120. Other conductor end lengths may be selected and a suitable length of the cavity 172 may be selected to ensure sufficient crimp length of the coil 120 within the cavity 172. The conductor end 162 may include a hole or a pair of holes 174 for inspecting the crimped conductor 120 within the cavity 172. The holes 174 may extend through the conductor end 162 from an outer surface and into the cavity 172 and may be positioned near a proximal end of the cavity 172. As such, when the conductor 120 is crimped in the cavity 172, a portion of the conductor 120 may be visible through the hole or holes 174 and the depth into the cavity 172 of the crimp connection may be ascertainable to assure sufficient crimp length.

The connector pin 112 can be made from one or more of several biocompatible conductor materials such as stainless steel 316L or a metal alloy MP35N, for example. The pin material may be selected to be biocompatible and suitably conduct and transmit electrical signals from an electrical stimulation device. The material together with the sizes of the pin 112 and the pin sleeve 122 (e.g., relative diameters and wall thicknesses) may be selected to suitably crimp the inner conductor or coil 120 therebetween such that a reliable crimp connection is provided that is both mechanically secure and through which electrical transmissions can be made. It is noted that the connector pin 112 may be engineered to have sufficient strength to withstand compression forces associated with assembly. For example, as can be appreciated from FIG. 3, the conductor end 162 of the pin 112 may be forced through the bore 118 of the connector insulator 116 into the bore 119 and the necked down portion 164 of the pin 112 may be suitably strong to withstand such a compression force without buckling or weakening. In an effort to more smoothly insert the pin 112, the distal end of the conductor end 162 may include an exterior taper 176 as shown in FIG. 4.

Figure 5:
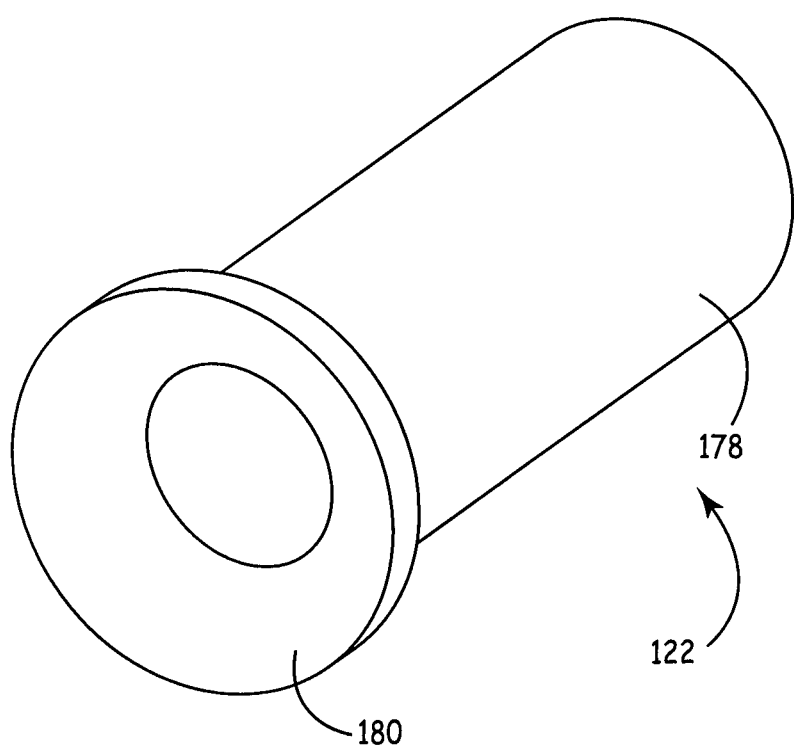
FIG. 5 shows a perspective view of a pin sleeve of the lead of FIG. 1 and FIG. 2.

A close-up view of the pin sleeve 122 is shown in FIG. 5. The pin sleeve 122 may be adapted for insertion a selected distance into the proximal end of the conductor or coil 120. As such, the pin sleeve 122 may include a sleeve portion 178 and a flare portion 180. The sleeve portion 178 may be substantially cylindrically shaped for insertion into the proximal end of the coil 120. The diameter of the sleeve portion 178 may be slightly larger than that of the coil 120 to create some connecting friction between the sleeve 122 and the coil 120 when the coil is sleeved over the sleeve portion 178. The diameter of the pin sleeve 122 may also be selected to suitably pinch or press the coil 120 against the inner surface of the cavity of the conductor end 162 of the pin 112 when crimping the coil 120. The sleeve portion 178 may have a length selected to sufficiently engage the coil 120 and hold the coil 120 when the coil 120 is crimped between the sleeve 178 and the inner surface of the conductor end 162 of the pin 112. The flare portion 180 of the sleeve 122 may be positioned on a proximal end of the sleeve 122 and may be configured to limit or stop the insertion distance of the sleeve 122 in the coil 120 and to prevent the sleeve 122 from passing too far into the coil 120 when crimping the coil 120. As such, the flared portion 180 may include a gradually increasing diameter beginning with the diameter of the sleeve portion 178 and extending to a diameter approximating the inner diameter of the conductor end 162 of the pin 112. It is noted that the proximal end of the pin sleeve 122 is shown as a flared portion in contrast to the more square or flange-like proximal end on the ring sleeve 136 of FIGS. 9A and 9B. The shape of the proximal ends of these parts 122, 136 may be selected based on whether the respective part is formed from tubing or bar stock. For example, if the part is formed from tubing, the proximal end may be flared like the pin sleeve 122 shown. However, if the part is formed from bar stock, the proximal end may be flange-like like the ring sleeve 136. Other fabrication techniques and approaches may also be used.

The inner diameter of the conductor end 162 of the pin 112 and the outer diameter of the sleeve portion 178 of the pin sleeve 122 may be selected to suitably crimp the inner conductor or coil 120 therebetween. For example, the pin sleeve 122 may have an outer diameter and the wire used for the inner coil 120 may have a thickness. The inner diameter of the cavity 172 may be selected to be slightly less than the outer diameter of the pin sleeve 122 plus twice the wire thickness. As such, when the pin sleeve 122 is inserted into the coil 120 and the pin sleeve 122 and conductor 120 are pressed into the cavity 172 of the conductor end 162 of the pin 112, the coil 120 may be crimped between the pin sleeve 122 and the inner surface of the cavity 172 of the conductor end 162 of the pin 112. Consideration may be given to the thicknesses and elasticity of the conductor end 162 of the pin and the sleeve 122 when selecting suitable relative diameters.

The inner conductor or coil 120 may be an electrically conductive member extending longitudinally along the lead 100. The conductor 120 may be in the shape of a coil or a tubular sleeve shape may be provided. The coil shape may provide flexibility to the lead and allow for maneuverability when placing the lead, for example. The inner conductor 120 may include a longitudinally extending bore along its length for receiving a stylet or other device.

As mentioned, the inner parts may be electrically isolated from the outer parts by a system of insulating parts. A close-up view of the connector insulator 116 is shown in FIGS. 6A and 6B. The connector insulator 116 may be configured for sleevably isolating the connector pin 112 and a portion of the inner conductor 120 from the outer parts. In addition, the connector insulator 116 may be configured for supporting all or a portion of the proximal seal 114. In this active lead embodiment, the connector insulator 116 may be configured for rotationally isolating the connector pin 112 from the proximal seal 114 such that the connector pin 112 may be rotated thereby rotating the inner conductor or coil 120 and controlling an active mechanism 106 on a distal end 104 of the lead 100.

As shown in FIGS. 6A and 6B, the connector insulator 116 may include a central body 182, a proximal extension 184, and a distal extension 186. The central body 182 may include a substantially cylindrically shaped body having an outer diameter. The distal extension 186 may also be substantially cylindrically shaped and may include an outer diameter smaller than that of the central body 182. The distal extension 186 may extend from the central body 182 in the distal direction from a set of cascading shoulders. An outer shoulder 188 may include a portion of the outer surface 129 of the central body 182 and a step surface 132 having a width. The width of the step surface 132 may define a diameter of a cylindrical inner shoulder surface 127 where the diameter of the inner shoulder surface 127 is less than the diameter of the central body 182 but larger than the diameter of the distal extension 186. The inner shoulder 190 may thus include this inner shoulder surface 127 and an additional step surface 128 having a width. The width of the additional step surface 128 may define the diameter of the distal extension 186. The distal tip of the distal extension 186 may include a tapered or chamferred tip 192 creating a conical shape for receiving the claw portion 126 of the insulator tubing 124. That is, as shown in FIG. 3, for example, the claw portion 126 of the insulator tubing 124 may be stretched, expanded, or otherwise distended over the distal extension 186 of the connector insulator 116. This relationship of the distended claw portion 126 being held away from the crimp connection of the inner conductor 120 may provide space for this connection and may help to avoid binding, pinching, or otherwise constricting the crimp connection at this location. As such, in the case of an active lead, the inner parts including the connector pin 112, the pin sleeve 122, and the inner conductor 120 may be free to rotate relative to the remaining parts without restriction.

The proximal extension 184 of the connector insulator 116 may extend from the proximal end of the central body 182 and may be substantially cylindrical with a diameter smaller than that of the central body 182. The transition between the central body 182 and the proximal extension 184 may define a proximal shoulder 194 opposite the cascading shoulders described. The outer surface of the proximal extension 184 may include one or more circumferential grooves 196. The proximal extension 184, in this active embodiment, may have a length substantially equal to the length of the proximal seal 114. As such, when the proximal seal 114 is positioned on the proximal extension 184 a distal end of the proximal seal 114 may abut the proximal shoulder 194 of the central body 182 and a proximal end of the proximal seal 114 may align with the proximal end of the connector insulator 116.

The connector insulator 116 may include center bore 118 with a diameter configured for receiving the necked-down portion 164 of the connector pin 112. The diameter of the bore 118 may be slightly larger than the necked-down portion 164 so as to allow rotation of the connector pin 112 relative to the connector insulator 116. In other embodiments lubrication and/or a bushing may be provided to offer further rotational freedom of the pin 112 relative to the connector insulator 116. The center bore 118 may extend from the proximal end of the insulator 116 to a point within the central body 182 of the insulator 116 where the center bore 118 may transition to a bore 119 with a larger diameter. The bore 119 with the larger diameter may accommodate the increased diameter of the conductor end 162 of the connector pin 112. The diameter of the bores 118, 119 may remain slightly larger than the respective portion of the connector pin 112 to allow rotation of the connector pin 112 relative to the connector insulator 116. The bore 119, with its larger diameter, may extend through the remaining portion of the central body 182 and through the distal extension 186 of the connector insulator 116.

The connector insulator 116 may be constructed from a bio-compatible grade of insulator material. This material may be selected to provide sufficient mechanical strength, elasticity, and insulation characteristics. For example, as described with respect to the connector pin 112, the conductor end 162 of the connector pin 112 may be pressed through the bore 118 of the connector insulator 116. As such, the connector insulator 116 may be made of a relatively strong yet elastic material allowing the pin 112 to be driven therethrough without loss of strength and without permanent deformation. In some embodiments, the connector insulator 116 may be made from a moldable thermoplastic such as polyurethane, polysulfone, or PEEK. Still other material may be selected to provide the suitable strength, elasticity, and insulation characteristics. While elastic, the connector insulator 116 may also be designed to secure the connector pin 112 and prevent the connector pin 112 from being removed or withdrawn from the proximal end of the lead 100. That is, a proximal shoulder 131 at the proximal end of the conductor end 162 may be provided to transition to the smaller diameter necked down portion 164. A surface 135 of the shoulder 131 may interact with an opposing surface 137 of shoulder 133 on the interior surface of the connector insulator 116. The shoulder 133 on the interior of the connector insulator 116 may be formed as the transition between the bore 118 and bore 119. The relative diameters of the necked down portion 164 and bore 118 and the relative diameters of the conductor end 162 and bore 119 may be selected to allow the connector pin 112 to rotate within the connector insulator 116. However, to prevent removal therefrom, the diameter of the conductor end 162 may be selected to be larger than the diameter of bore 118. In addition, the material of connector insulator 116 may be selected to be rigid enough to prevent withdrawal of the connector pin 112 under withdrawal loads or strengths specified by the IS-1 specification, for example.

Figure 7B:
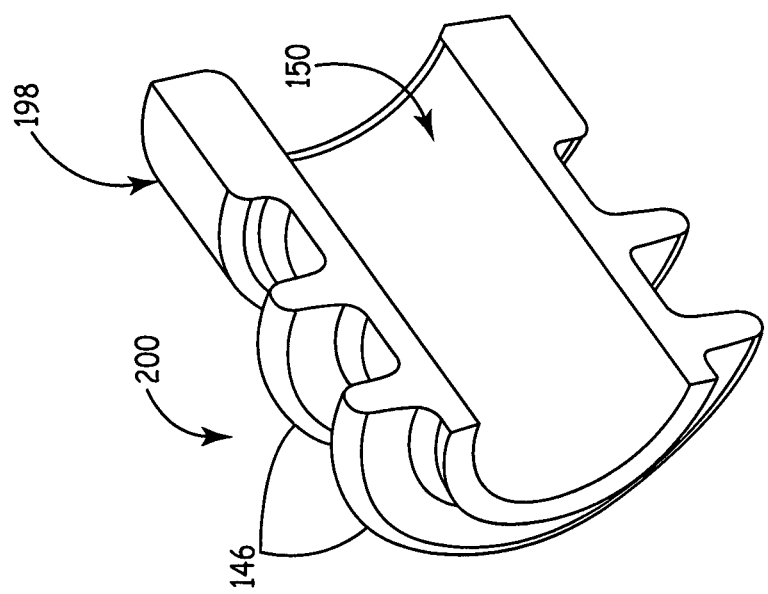
FIGS. 7A and 7B show a perspective view and a perspective cross-sectional view, respectively, of a proximal seal of the lead of FIG. 1.
Figure 7A:
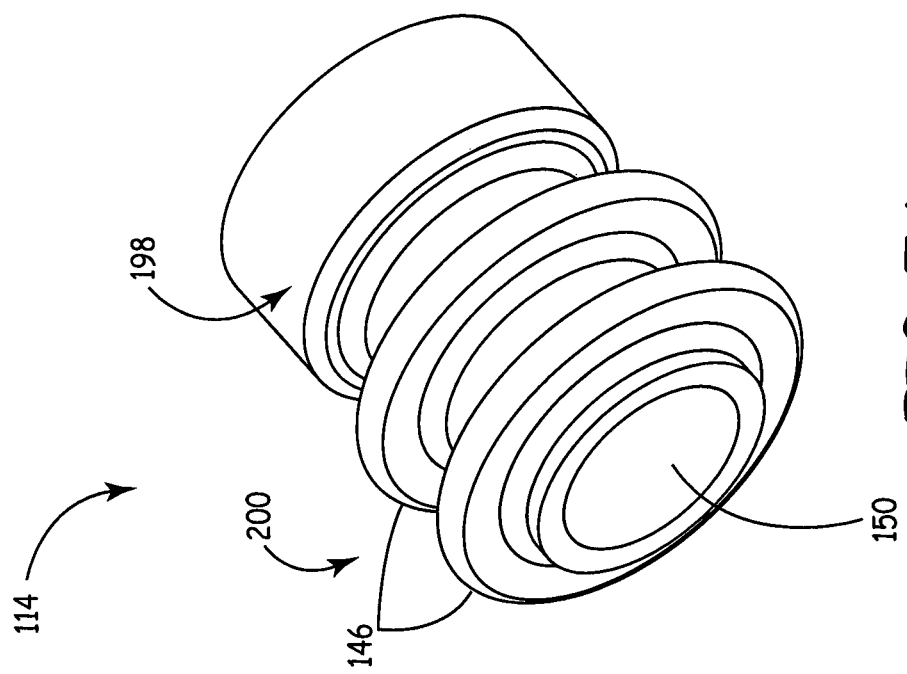

The proximal seal 114 may be configured for secured placement on the connector insulator 116 and for sealingly engaging a socket on an electrical stimulation device. In addition, the proximal seal 114 may function, together with the connector insulator 116, to electrically isolate and prevent crosstalk between the ring connector 130 and the connector pin 112. As shown in FIGS. 7A and 7B, the proximal seal 114 may include a flushing portion 198 and a sealing portion 200. The flushing portion 198 may be distal to the sealing portion 200 and may function to encompass the connector insulator 116 and abut the central body 182 thereof. The flushing portion 198 may be substantially cylindrical with an outer diameter substantially matching the outer diameter of the central body 182 thereby being flush therewith. The sealing portion 200 may be proximal to the flushing portion 198 and may also be substantially cylindrical with an outer diameter slightly smaller than the flushing portion 198. The sealing portion 200 may include one or more (e.g., two) circumferentially extending ribs 146 protruding from the outer surface of the sealing portion 200. The ribs 146 may extend from the sealing portion 200 such that the outer surface or tip of the ribs 146 defines a diameter larger than the flushing portion 198. The ribs 146 may be adapted to engage a cylindrical socket and may have an outer diameter at least slightly larger than the diameter of the socket so as to sealingly engage an inner surface of the socket and prevent fluids or other matter from traveling into the socket and reaching the connector pin 112 or otherwise leaking into the electrical stimulation device.

The proximal seal 114 may include a bore 150 extending from its proximal end to its distal end and the diameter of the bore 150 may be substantially equal to the outer diameter of the proximal extension 184 of the connector insulator 116. In some embodiments, the proximal seal 114 may be made of a resilient material and the bore diameter may be slightly smaller than the outer diameter of the proximal extension 184 of the connector insulator 116 such that the proximal seal may be stretched to receive the connector insulator 116 thereby compressively receiving the connector insulator 116 therein. The proximal seal 114 may be made from a suitably resilient material to compressively seal the proximal end 102 of the lead 100 with the electrical stimulation device. In some embodiments, the seal 114 may be a biocompatible silicone, for example. Still other materials may be selected to suitably seal the proximal end 102 of the lead 100 with the electrical stimulation device and also be compatible with the body.

The insulator tubing 124 shown in FIG. 3 may function to electrically isolate portions of the inner parts from the outer parts. Along some portions of the lead, the insulator tubing 124 may function together with the connector insulator 116 to provide the electrical isolation. As shown, a portion of each of the inner parts including the connector pin 112 (i.e., the conductor end 162 thereof), the inner coil 120, and the pin sleeve 122 may be separated from the outer parts by the inner insulator tubing 124. Near the proximal end of the conductor 120, the distal extension 186 of the connector insulator 116 also isolates these elements. The insulator tubing 124 may be substantially tube-like in shape defining an inner lumen having a diameter slightly larger than the outer diameter of the inner conductor or coil 120. As such, in the case of an active lead, the inner conductor 120 may be relatively free to rotate within the insulator tubing 124. The insulator tubing 124 may be made of an insulating material so as to electrically isolate the enclosed components or features from the components or features outside the tubing 124. The insulator tubing 124 may include a flared or claw portion 126 at its proximal end for receiving the distal extension 186 of the connector insulator 116. In some embodiments, this portion is a flared or expanded to fit over the distal extension 186 of the connector insulator 116. As previously mentioned, this flared or claw portion 126 held open by the distal extension 186 of the connector insulator 116 may help to prevent binding of the inner parts by providing space for the crimp connection. Within the distal extension 186 of the connector insulator 116, the conductor end 162 of the pin connector 112, the pin sleeve 122, and the proximal end of the conductor or coil 120 may be arranged and thus electrically isolated from components or features outside the claw portion 126.

Having described the inner parts and the isolation thereof by the insulator tubing 124 and the connector insulator 116, the outer parts may now be described. As shown in FIG. 3, the outer part may include the ring connector 130, an outer conductor or coil 134, and a ring sleeve 136.

The ring connector 130 may be configured to provide an exposed surface for electrical communication with an electrical stimulation device. The ring connector 130 may also be configured for axially and rotationally securing the outer parts to the connector insulator 116.

A close-up view of the ring connector 130 is shown in FIGS. 8A and 8B. The ring connector 130 may include a band portion 204, a slot portion 206, and a crimp portion 208. The band portion 204 may form an exposed conductive band near the proximal end 102 of the lead 100 that is distal to the connector pin 112. The band portion 204 may be configured for electrical communication with a portion of a socket of an electrical stimulation device and the diameter of the band portion 204 may be selected to suitably engage electrical conductors within the socket.

The band portion 204 may include a substantially cylindrical shape with an outer diameter matching that of the central body 182 of the connector insulator 116. The band portion 204 may include an inner cavity 210 configured to receive the distal extension 186 of the connector insulator 116. More particularly, the inner cavity 210 of the band portion 204 may have a diameter substantially equal to or slightly smaller than the outer diameter of the cylindrical inner shoulder surface 127 on the connector insulator 116. As such, the band portion 204 may be sleeved over the claw portion 126 positioned on the distal extension 186 and may frictionally engage the cylindrical inner shoulder surface 127 to secure the ring connector 130 to the connector insulator 116. In this manner, the concentric assembly of the several parts of the system may be maintained. The band portion 204 of the ring connector 130 may thus and abut the step surface 132 causing the outer surface of the band portion 204 to be flush with the central body 182 of the connector insulator 116. The band portion 204 may have a length slightly greater than the length of the distal extension 186 of the connector insulator 116.

The slot portion 206 of the ring connector 130 may be arranged distally relative to the band portion 204 and may be substantially cylindrically shaped with a diameter smaller than the band portion 204. The slot portion 206 may be configured for encroaching on the insulator tubing 124 and, as such, the slot portion 206 may include an inner diameter similar to or slightly larger than the outer diameter of the insulator tubing 124. The smaller outer diameter of the slot portion 206 may allow for an inwardly projecting rib 212 from the boot seal 140 to nest in the slot 206 formed thereby. The rib 212 may be held in position longitudinally by two opposing surfaces 142 and 143. The slot portion 206 may include one or more holes 214 for placement of adhesive to secure the ring connector 130, the insulator tubing 124, and the boot seal 140 together.

The crimp portion 208 may be arranged distally to the slot portion 206 and may be substantially cylindrically shaped with an outer diameter larger than the slot portion 206 and smaller than the band portion 204. Like the conductor end 162 of the connector pin 112, the crimp portion 208 of the ring connector 130 may be configured for crimping of the outer conductor 134 therein. As such, the crimp portion 208 may define a crimp zone or cavity 216 therein. The cavity or crimp zone 216 may include an inner diameter selected in conjunction with the ring sleeve 136 to suitably crimp the outer conductor 134 therein. That is, the ring sleeve 136 may have an outer diameter and the outer conductor 134 may include a wire thickness. The inner diameter of the crimp zone or cavity 216 may be selected to be equal to or slightly smaller than the outer diameter of the ring sleeve 136 plus twice the wire thickness, for example. Like the inner conductor crimp connection, the material strength, diameter, thickness, and elasticity may be considered when selecting the relative diameters for crimping the outer conductor 134. The crimp portion 206 of the ring connector 130 may include a length equal to or slightly larger than the ring sleeve 136 such that a sufficient length of the outer conductor 134 may be crimped therein. In some embodiments the crimp portion 208 of the ring connector 130 may include circumferentially extending grooves 218 extending around its circumferential outer surface for engagement by the boot seal 140. The crimp portion 208 may also include a hole or a pair of holes 220 for inspecting the crimped conductor 134 within the cavity 216. The holes 220 may extend through the crimp portion 208 from an outer surface and into the cavity 216 and may be positioned near a proximal end of the cavity 216. As such, when the conductor 134 is crimped in the cavity 216, a portion of the conductor 134 may be visible through the hole or holes 220 and the depth into the cavity 216 of the crimp connection may be ascertainable to assure sufficient crimp length.

Like the connector pin 112, the ring connector 130 may be constructed of a bio-compatible conductive material. For example, the ring connector 130 may be made from stainless steel 316L or a metal alloy MP35N, for example. Other materials may also be used and may be selected to provide suitable biocompatibility and conductivity. Additionally, as with the connector pin 112, the material and dimensions (e.g., relative diameters and wall thicknesses) may be selected to suitably allow for a crimp connection to the outer conductor or coil 134 that is both mechanically secure and also effectively transmits electrical signals.

The outer conductor or coil 134 may be the same or similar to the inner conductor or coil 120. However, the outer conductor or coil 134 may include a diameter larger than the inner conductor or coil 120. The diameter of the outer conductor or coil 134 may be selected such that the inner conductor or coil 120 and the insulator tubing 124 may be received therein. As such, the outer conductor or coil 134 may have a diameter equal to or slightly greater than an outside diameter of the inner conductor or coil 120 plus twice the thickness of the insulator tubing 124. In some embodiments, the diameter of the outer conductor or coil 134 may be selected to allow non-constricted rotation of the inner coil 120 within the insulator tubing 124 for controlling an active mechanism 106 on a distal end 104 of the lead 100, for example. In other embodiments, the diameter of the outer coil 134 may be more constricting on the insulator tubing 124 and the inner coil 120.

The ring sleeve 136, like the pin sleeve 122 may be configured for crimping the outer conductor or coil 134 within the crimp portion 208 of the ring connector 130. As shown in FIGS. 9A and 9B, the ring sleeve 136 may include sleeve portion 222 and a flare or rib portion 224 for controlling the depth within the coil 134 that the ring sleeve 136 extends. The sleeve portion 222 may be a substantially cylindrical portion with an outer diameter slightly larger than an inner diameter of the outer coil 134. As such, when inserted into a proximal end of the outer coil 134, some frictional engagement between the ring sleeve 136 and the outer coil 134 may be provided. The flare or rib portion 224 may be positioned on the proximal end of the sleeve portion 222 and may include a diameter larger than that of the sleeve portion 222 for abutting the end of the outer conductor or coil 134 and resisting advancement of the ring sleeve 136 beyond the proximal end of the outer conductor or coil 134. The diameter of the flare or rib 224 may be selected to be slightly less than the inner diameter of the crimp portion 208 of the ring connector 130 so as to avoid inhibiting the pinching or crimping of the coil 134 between the sleeve portion 222 and the inner surface of the crimp portion 208 of the ring connector 130. As discussed with respect to the pin sleeve 122, the shape of the proximal end of the pin sleeve 122 and the ring sleeve 136 may depend in part on the type of raw material used to form the respective part. For example, if tubing is used, the proximal end may be flared, while, if bar stock is used, the proximal end may be more square in cross-section or flange-like. Other geometries may also be provided to stop the sleeves from overly advancing into the proximal end of the respective coils 120, 134.

Figure 10A:
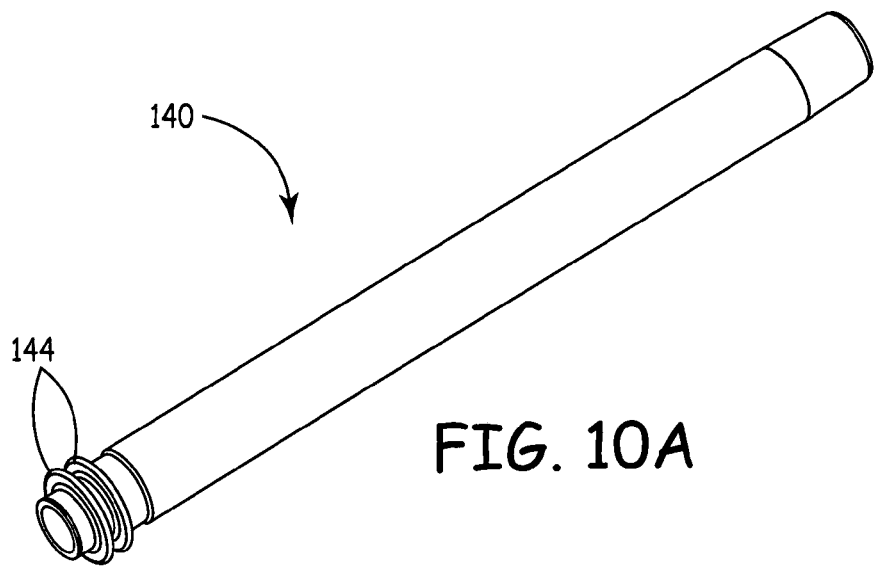
FIGS. 10A and 10B show a perspective view and a perspective cross-sectional view, respectively, of a boot seal of the lead of FIG. 1 and FIG. 2.
Figure 10B:
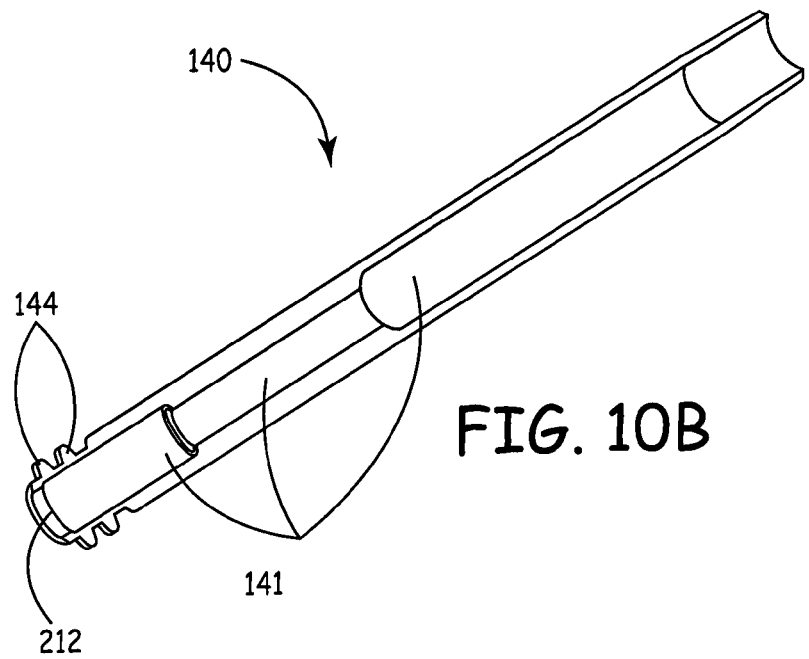

The boot seal 140 is shown in FIGS. 10A and 10B. The boot seal 140 may be configured for encompassing the distal end of the ring connector 130 and for sealing the ring connector 130 from entry of fluids. For example, when the proximal end 102 of the lead 100 is inserted into a socket of an electrical stimulation device, the boot seal 140 may prevent fluids or other material from entering the socket and interfering with the ring connector 130 or other portions of the electrical stimulation device. As such, the boot seal 140, like the proximal seal 114, may include one or more circumferentially extending ribs 144 protruding from its outer surface. The ribs 144 may be adapted to engage a cylindrical socket and may have an outer diameter at least slightly larger than the diameter of the socket so as to sealingly engage an inner surface of the socket and prevent fluids or other matter from traveling into the socket and reaching the ring connector 130 or otherwise leaking into the electrical stimulation device.

The boot seal 140 may be relatively long and may provide a grip for the surgeon or other installer for handling the proximal end 102 of the lead 100. The boot seal 140 may include a bore 141 extending from its proximal end to its distal end and the diameter of the bore may vary along the length of the seal 140. The proximal end of the bore 141 may be relatively enlarged to house the crimp portion 208 of the ring connector 130. Moving distally, the diameter of the bore 141 may be reduced an may be sized just slightly larger than the outer diameter of the outer coil 134. Moving still further distally, the diameter of the bore 141 may again be enlarged. In this region, the boot seal may be enlarged due to an outer insulator tubing and for the application of a lead label and/or serial number. The proximal end of the boot seal 140 may include an inwardly protruding rib 212 for arrangement in the slot portion 206 of the ring connector 130 thereby securing the longitudinal position of the boot seal 140. Like the proximal seal 114, the boot seal 140 may be made from a biocompatible silicone to resiliently engage and seal the lead 100 relative to the electrical stimulation device. Other materials may also be used.

Referring again to FIG. 3, the assembled proximal end of the lead may be described. As shown, the electrically conductive connector pin 112 may extend through and may be rotatably disposed in a center bore 150 of a proximal seal 114 and a center bore 118 of a connector insulator 116. The necked-down portion 164 of the connector pin 112 may be arranged in the center bore 118 and the electrically conductive inner conductor or inner coil 120 may be crimped to the conductor end 162 of the connector pin 112 by the pin sleeve 122. The inner insulator tubing 124 may extend over the inner coil 120 and the claw portion 126 thereof may be sleeved onto the distal extension 186 of the connector insulator 116 to abut the inner shoulder 190 of the cascading shoulders and having an outer surface substantially flush with the cylindrical outer surface 127 of the inner shoulder 190. As such, the connector pin 112, the crimp connection, and the inner coil 120 may be substantially fully insulated along its length by the connector insulator 116 and the insulator tubing 124. However, the inner conductor 120 may be exposed via an electrode at the distal end 104 for treatment and the connector pin 112 may be exposed at the proximal end 102 for electrical communication with an electrical stimulation device. The proximal seal 114 may be arranged on the connector insulator and the outwardly projecting ribs 146 may engage a socket on an electrical stimulation device to prevent fluid or other liquid from being in contact with the connector pin 112.

The band portion 204 of the ring connector 130 may extend over the claw portion 126 of the insulator tubing 124 and may abut the outer shoulder 188 of the cascading shoulders on the connector insulator 116. As shown, the outer surface of the band portion 204 of the ring connector 130 may be flush with the outer surface 129 of the central body 182 of the connector insulator 116. The outer conductor or outer coil 134 may be arranged to sleevably receive the inner coil 120 and insulator tubing 124. The outer conductor or coil 134 may be crimped to the ring connector 130 by a ring sleeve 136, thereby electrically connecting to the ring connector 130. The boot seal 140 may be positioned over the outer coil 134 and an inwardly protruding rib 212 thereof may engage a slot portion 206 of the ring connector thereby securing the position of the boot seal 140 relative to the ring connector 130. The crimped outer coil 134 and portions of the ring connector 130 may be disposed within a center bore 141 of the boot seal 140. Like the proximal seal 114, the outwardly projecting ribs 144 of the boot seal 140 may engage a socket on an electrical stimulation to prevent body fluid or other liquid from being in contact with the ring connector 130 or otherwise entering the electrical stimulation device.

As shown in FIG. 3, the necked-down portion 164 of the pin 112 may extend through the center bore 150 of the proximal seal 114. The necked-down portion 164 may be separated from the inner surface of the center bore 150 by the proximal extension 184 of the connector insulator 116. As such, an inner surface 154 of the connector insulator 116 may provide rotational bearing for the connector pin 112 such that the connector pin 112 may rotate relative to the connector insulator 116 and proximal seal 114. Rotation of the connector pin 112 may drive rotation of the inner coil 120, thereby rotating the mechanism 106 disposed at the distal end 104 of the lead 100. The lead 100 shown may be referred to as an active lead, and the mechanism 106 may be referred to as an active mechanism. It is appreciated that other suitable rotatable connection means may be used between the inner coil 120 and the connector pin 112 without departing from the scope of the present invention.

Accordingly, the connector pin 112 may be electrically connected to the inner coil 120, and the ring connector 130 may be electrically connected to the outer coil 134. In operation of the present invention, electrical signals may be sent from the proximal end 102 to the distal end 104 via the connector pin 112 and the inner coil 120, and via the ring connector 130 and the outer coil 134. The inner coil 120 may be electrically insulated from the outer coil 134 by the inner insulator tubing 124. The ring connector 130 may be electrically insulated from the inner coil 120 by the inner insulator tubing 124 and the connector insulator 116. The connector pin 112 may be electrically insulated from the ring connector 130 by the proximal seal 114 and the connector insulator 116. The connector pin 112 may be prevented from being in contact with fluid or other liquid by the ribs 146 of the proximal seal 114. The ring connector 130 may be prevented from being in contact with fluid or other liquid by the ribs 144 of the boot seal 140.

FIG. 11 illustrates a cross-sectional view of the proximal end 402 of one embodiment of the implantable medical electrical lead 400 with the passive mechanism 406 in accordance with the principles of the present invention. The reference numerals used in FIG. 11 correspond to the reference numbers used in FIG. 3 to reflect the similar parts and components, except the first digit of each reference numeral.

Figure 12B:
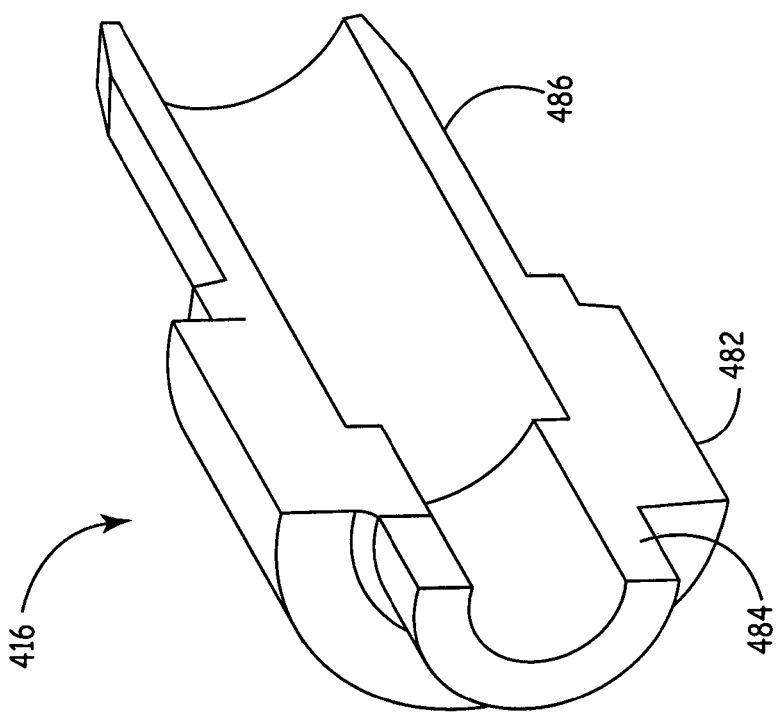
FIGS. 12A and 12B show a perspective view and a perspective cross-sectional view, respectively, of a connector insulator of the lead of FIG. 2.
Figure 12A:
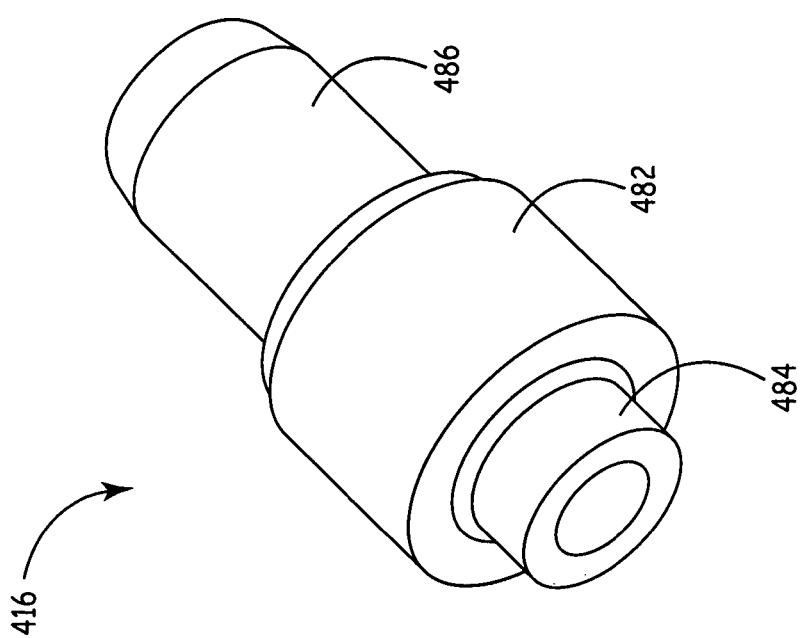
Figure 13B:
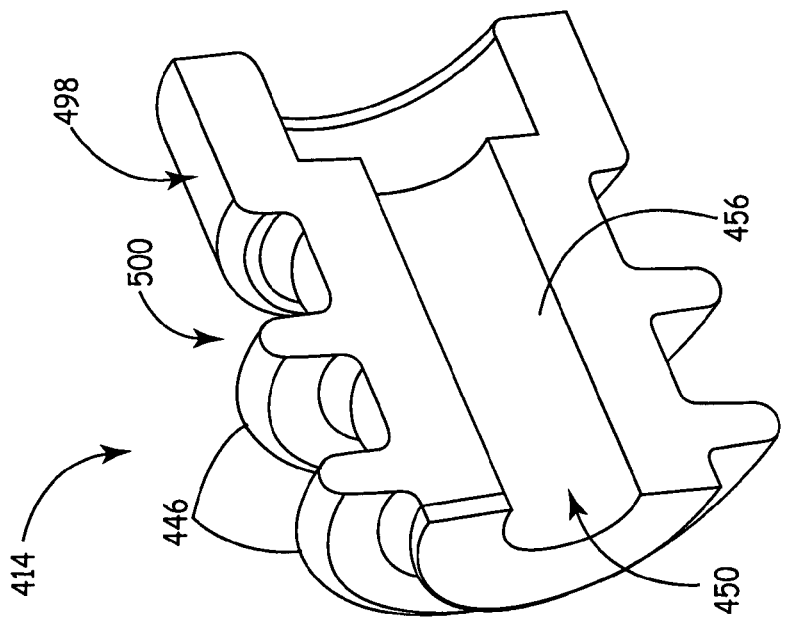
FIGS. 13A and 13B show a perspective view and a perspective cross-sectional view, respectively, of a proximal seal of the lead of FIG. 2.
Figure 13A:
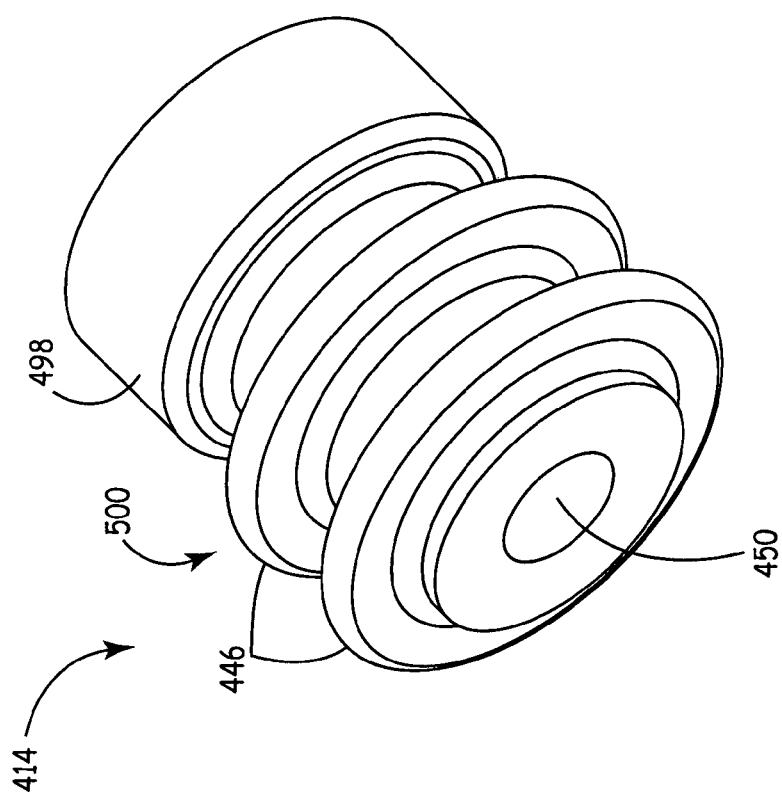

Accordingly, in the embodiment shown in FIG. 11, the design of the proximal end 402 of the lead 400 is very similar to the design of the proximal end 102 of the lead 100, except that a connector insulator 416 includes a much shorter proximal extension 484. As shown, in detail in FIGS. 12A and 12B, connector insulator 416 may be similar to the connector insulator 116 in many respects. For example, the central body 482 and distal extension 486 may be substantially the same. However, the proximal extension 484 may extends inside the center bore 450 of the proximal seal 414 a shorter distance than proximal extension 184. In contrast to FIG. 3, the proximal extension 484 shown in FIG. 11 extends partially through the bore 450, but not fully through the bore 450. The remaining portion of the bore 450, as shown in FIGS. 11, 13A and 13B, has a smaller diameter that encroaches the outer diameter of the necked-down portion 464 of the connector pin 412. In this embodiment, rather than allowing for rotation of the pin 412, the connector pin 412 may be fixedly connected to an inner surface 456 of the proximal seal 414 by medical adhesive or other suitable bio-adaptable adhesive equivalence. In this embodiment, the connector pin 412 may not be free to rotate relative to the other portions of the lead 400 and as such, the inner conductor or coil 420 may not be rotated to cause rotation of the mechanism 406 disposed at the distal end 404 of the lead 400. This lead 400 may be referred to as a passive lead, and the mechanism 406 at the distal end may be referred to as a passive mechanism.

As a result, one of the advantages of the present invention is that most of the parts and components of active and passive leads can be shared, which significantly reduces the cost of tooling, manufacturing, and assembling. For example, in comparing FIGS. 3 and 11, all of the inner parts 112/412, 122/422, 120/420 and the outer parts 130/430, 136/436, 134/434 are the same. The insulator tubing 124/424 is also the same. The difference between the parts of FIGS. 3 and 11 include differing proximal seals 114, 414 and the differing connector insulators 116, 416. Accordingly, of the ten parts used to construct the proximal end 102, 402 of the active or passive leads 100, 400, two of the ten may be modified to transition from an active to a passive lead.

These and other features of the present invention will become apparent to those skilled in the art from the above description. As it will be realized, the invention is capable of modifications in various obvious aspects, all without departing from the spirit and scope of the present invention. Also, it is appreciated that the configurations, shapes, forms, sizes, materials, and assembly of the above-mentioned leads and the configurations, shapes, forms, sizes, materials, and assembly at a distal end with a passive or active mechanism can be implemented in various ways without departing from the scope of the present invention.

What is claimed is:

1. An implantable lead including a first conductor and a second conductor, the lead comprising:
    a connector insulator having a center bore and a central body, wherein the central body has an outer surface as a portion of an outer surface of the lead;
    a unitary connector pin fixedly disposed in the center bore of the connector insulator such that the unitary connector pin is non-rotatable within the center bore, the unitary connector pin having a socket end configured for insertion into an electrical stimulation device and a conductor end electrically crimped to the first conductor; and
    a unitary ring connector having a band portion concentrically arranged around and insulated from the conductor end of the unitary connector pin by the connector insulator and a crimp portion electrically crimped to the second conductor, wherein the band portion of the ring connector and the central body of the connector insulator abut and have matching outer diameters.

2. The implantable lead of claim 1, further comprising a passive mechanism arranged on a distal end of the implantable lead.

3. The implantable lead of claim 2, wherein the passive mechanism includes an anchor-type fixation mechanism having a plurality of tines.

4. The implantable lead of claim 1, wherein the unitary connector pin further comprises a necked-down portion arranged between the socket end and the conductor end.

5. The implantable lead of claim 1, wherein the conductor end includes a crimp cavity with an inner surface and a proximal end of the first conductor is positioned in the crimp cavity.

6. The implantable lead of claim 5, further comprising a pin sleeve, wherein the proximal end of the first conductor sleeves over the pin sleeve and is thereby crimped against the inner surface when positioned in the crimp cavity.

7. The implantable lead of claim 1, wherein the crimp portion of the unitary ring includes a crimp cavity with an inner surface and a distal end of the second conductor is positioned in the crimp cavity.

8. The implantable lead of claim 7, further comprising a ring sleeve positioned in the crimp cavity; wherein a proximal end of the second conductor sleeves over an outer surface of the ring sleeve and a crimp connection is provided to the proximal end of the second conductor against the inner surface.

9. The implantable lead of claim 1, wherein the connector insulator further comprises a distal extension extending within the band portion of the ring connector.

10. The implantable lead of claim 1, wherein the connector insulator includes a shoulder that abuts a proximal end of the band portion of the ring connector such that the ring connector is held in concentric relationship with the connector insulator.

11. The implantable lead of claim 1, wherein the connector insulator includes a proximal extension.

12. The implantable lead of claim 11, further comprising a proximal seal arranged on the proximal extension of the connector insulator, wherein the proximal seal is partially isolated from the connector pin by the proximal extension and partially engaged with the connector pin.

13. The implantable lead of claim 12, wherein the proximal seal comprises a plurality of circumferentially extending sealing ribs, the proximal seal prevents liquid from contacting the connector pin, and the proximal seal provides electrical insulation between the ring connector and the connector pin in conjunction with the connector insulator.

14. The implantable lead of claim 1, wherein the unitary ring connector includes an annular notch portion defined in an outer surface of the unitary ring connector between the band portion and the crimp portion of the ring connector, the annular notch having an outer diameter that is smaller than an outer diameter of the band portion and the crimp portion.

15. The implantable lead of claim 14, further comprising a longitudinally extended boot seal having an inwardly projecting rib that engages the notch portion of the ring connector, the longitudinally extended boot seal being disposed over the crimp portion of the ring connector.

16. The implantable lead of claim 15, wherein the boot seal comprises a plurality of circumferentially extending sealing ribs and prevents fluid from contacting the crimp portion of the ring connector.

\* \* \* \* \*